United States Patent
Atanasoska et al.

(10) Patent No.: US 9,314,551 B2
(45) Date of Patent: Apr. 19, 2016

(54) BLOCK COPOLYMER-COATED ENDOPROSTHESIS

(75) Inventors: Liliana Atanasoska, Edina, MN (US); Mourad Rahi, Roseville, MN (US); Robert W. Warner, Woodbury, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 400 days.

(21) Appl. No.: 13/105,473

(22) Filed: May 11, 2011

(65) Prior Publication Data

US 2011/0282430 A1 Nov. 17, 2011

Related U.S. Application Data

(60) Provisional application No. 61/334,746, filed on May 14, 2010.

(51) Int. Cl.
| | |
|---|---|
| A61F 2/82 | (2013.01) |
| A61L 31/14 | (2006.01) |
| A61L 31/02 | (2006.01) |
| A61L 31/06 | (2006.01) |
| A61L 31/10 | (2006.01) |
| A61L 31/16 | (2006.01) |

(52) U.S. Cl.
CPC .............. *A61L 31/148* (2013.01); *A61L 31/022* (2013.01); *A61L 31/06* (2013.01); *A61L 31/10* (2013.01); *A61L 31/16* (2013.01); *A61L 2300/416* (2013.01)

(58) Field of Classification Search
CPC ....... A61L 31/022; A61L 31/16; A61L 31/06; A61L 31/10; A61L 2300/416; A61L 31/148; A61F 2250/0067; A61F 2250/0068
USPC ........................................ 623/1.15, 1.42–1.43
See application file for complete search history.

(56) References Cited

U.S. PATENT DOCUMENTS

| | | | |
|---|---|---|---|
| 4,897,255 A | | 1/1990 | Fritzberg et al. |
| 5,195,969 A | | 3/1993 | Wang et al. |
| 5,270,086 A | | 12/1993 | Hamlin |
| 5,366,504 A | | 11/1994 | Andersen et al. |
| 5,449,382 A | * | 9/1995 | Dayton .................. 623/1.15 |
| 5,674,242 A | | 10/1997 | Phan et al. |
| 5,733,925 A | | 3/1998 | Kunz et al. |
| 5,741,329 A | * | 4/1998 | Agrawal ............. A61L 27/50 424/423 |

(Continued)

FOREIGN PATENT DOCUMENTS

WO 2007/082304 7/2007

OTHER PUBLICATIONS

Zheng et al, "The in vivo and in vitro degradation behavior of poly(trimethylene carbonante)", (Mar. 2006), Biomaterials, vol. 27, Issue 9, pp. 1741-1748.*

(Continued)

*Primary Examiner* — Paul Prebilic
(74) *Attorney, Agent, or Firm* — Seager, Tufte & Wickhem LLP

(57) ABSTRACT

In embodiments, a stent includes a copolymer having a modulus of about 10 MPa or less and exhibiting hydrolytic degradation substantially by surface erosion. For example, the copolymer can include elastic segments formed of trimethyl carbonate polymer or copolymer, and rigid segments formed of a lactide, glycolide, ε-caprolactone polymer or copolymer.

11 Claims, 4 Drawing Sheets

(56) References Cited

U.S. PATENT DOCUMENTS

| | | | |
|---|---|---|---|
| 6,153,252 A * | 11/2000 | Hossainy et al. | 427/2.3 |
| 6,287,332 B1 | 9/2001 | Bolz et al. | |
| 6,368,658 B1 | 4/2002 | Schwarz et al. | |
| 6,676,987 B2 | 1/2004 | Zhong et al. | |
| 6,726,712 B1 | 4/2004 | Raeder-Devens et al. | |
| 6,794,485 B2 | 9/2004 | Shalaby et al. | |
| 6,830,747 B2 * | 12/2004 | Lang | A61K 47/34 424/78.17 |
| 7,435,255 B1 * | 10/2008 | Rao | 623/1.42 |
| 7,462,366 B2 | 12/2008 | Lanphere et al. | |
| 7,722,894 B2 | 5/2010 | Wang et al. | |
| 7,947,368 B2 | 5/2011 | Song | |
| 7,976,936 B2 | 7/2011 | Sahatjian et al. | |
| 8,012,454 B2 | 9/2011 | Rioux et al. | |
| 8,293,260 B2 * | 10/2012 | Wang | 424/422 |
| 2002/0004060 A1 | 1/2002 | Heublein et al. | |
| 2002/0188277 A1 * | 12/2002 | Roorda et al. | 604/523 |
| 2003/0040790 A1 * | 2/2003 | Furst | 623/1.11 |
| 2003/0118692 A1 * | 6/2003 | Wang et al. | 426/6 |
| 2003/0120029 A1 * | 6/2003 | Shalaby et al. | 528/310 |
| 2003/0208259 A1 * | 11/2003 | Penhasi | 623/1.15 |
| 2004/0047909 A1 * | 3/2004 | Ragheb et al. | 424/471 |
| 2004/0076582 A1 | 4/2004 | Dimatteo et al. | |
| 2004/0234575 A1 | 11/2004 | Horres et al. | |
| 2005/0171593 A1 * | 8/2005 | Whirley et al. | 623/1.13 |
| 2005/0209680 A1 * | 9/2005 | Gale et al. | 623/1.15 |
| 2005/0251249 A1 * | 11/2005 | Sahatjian et al. | 623/1.46 |
| 2007/0141099 A1 | 6/2007 | Buiser et al. | |
| 2008/0306592 A1 * | 12/2008 | Wang | 623/11.11 |
| 2009/0030507 A1 * | 1/2009 | Klocke et al. | 623/1.46 |
| 2009/0099652 A1 * | 4/2009 | Granada et al. | 623/1.46 |
| 2009/0306769 A1 * | 12/2009 | Schewe | A61M 25/1029 623/1.34 |
| 2010/0036476 A1 * | 2/2010 | Ameer et al. | 623/1.13 |
| 2011/0060398 A1 * | 3/2011 | Tupil et al. | 623/1.15 |
| 2011/0264190 A1 * | 10/2011 | McClain et al. | 623/1.11 |

OTHER PUBLICATIONS

Gunatillake et al, "Biodegradable Synthetic Polymers for Tissue Engineering", (May 2003), European Cells and Materials, vol. 5, pp. 1-16.*

U.S. Appl. No. 13/105,488, Warner et al.

Bat et al., "Trimethylene Carbonate and E-Caprolactone Based (co)Polymer Networks: Mechanical Properties and Enzymatic Degradation," Biomacromolecules, vol. 9, pp. 3208-3215, (2008).

Internatioinal Search Report and Written Opinion issued by the European Patent Office on Aug. 9, 2011 in the PCT application PCT/US2011/036018, filed on May 11, 2011.

Ishida et al., "Endothelial Lipase Modulates Susceptibility to Atherosclerosis in Apolipoprotein-E-deficient Mice," The Journal of Biological Chemistry, vol. 279, No. 43, pp. 45085-45092, Oct. 22, 2004.

Kickelbick, "Concepts for the incorporation of inorganic building blocks into organic polymers on a nanoscale," Progress in Polymer Science, vol. 28, pp. 81-114, (2003).

Li et al., "Preparation and characterization of maleic anhydride-functionalized syndiotactic polystyrene," Polymer, vol. 43, pp. 5455-5461, (2002).

Park et al., "Microstructural change and precipitation hardeningin melt-spun Mg—X—Ca alloys," Science and Technology of Advanced Materials, vol. 2, pp. 73-78, (2001).

Wischke et al., "Evalution of a degradable shape-memory polymer network at matrix for controlled drug release," Journal of Controlled Release, vol. 138, No. 3, pp. 243-250, Sep. 15, 2009.

International Preliminary Report on Patentability issued on Nov. 29, 2012, in the PCT application PCT/US2011/036018, filed on May 11, 2011, (10 pages).

* cited by examiner

BLOCK COPOLYMER-COATED ENDOPROSTHESIS

CROSS-REFERENCE TO RELATED APPLICATION

This application claims priority under 35 USC §119(e) to U.S. Provisional Patent Application Ser. No. 61/334,746, filed on May 14, 2010, the entire contents of which are hereby incorporated by reference.

TECHNICAL FIELD

The present invention relates to endoprostheses, and more particularly to stents.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism can include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

It is sometimes desirable for an implanted endoprosthesis to erode over time within the passageway. For example, a fully erodable endoprosthesis does not remain as a permanent object in the body, which may help the passageway recover to its natural condition. Erodible endoprostheses can be formed from, e.g., a polymeric material, such as polylactic acid, or from a metallic material such as magnesium, iron or an alloy thereof.

SUMMARY

The present invention is directed to an endoprosthesis, such as, for example, a biodegradable stent.

In an aspect, the invention features a stent including a copolymer having a modulus of about 10 MPa or less and exhibiting degradation substantially by surface erosion over a period of about 20 days or more.

Embodiments may include one or more of the following features.

The copolymer can include a therapeutic agent. In some embodiments, the copolymer is a coating on a metal stent body. The metal can be a biodegradable metal, such as Mg, Fe, or an alloy thereof. The metal can include cobalt and chromium. The copolymer may be a coating on a polymeric stent body. The copolymer can include elastic segments formed of trimethyl carbonate polymer or copolymer, and rigid segments formed of a lactide, glycolide or E-coprolactone polymer or copolymer. The copolymer can include rigid segments and flexible segments, and the rigid segments can have an elastic modulus of about 200 MPa or more. The rigid segments can exhibit hydrolytic degradation by bulk erosion. The flexible segments can be relatively resistant to hydrolytic degradation and can be susceptible to enzymatic surface degradation. The degradation enzyme can include lipases. The copolymer can be functionalized with maleic anhydride. The copolymer can be crosslinked. The copolymer can be a layer on a biostable metal stent body, such as a stainless steel stent body or a Co—Cr stent body. The layer can be on the abluminal surface of the stent body.

Embodiments may include one or more of the following advantages. A stent is provided with advantageous drug delivery characteristics, mechanical properties and biodegradability. The stent can include a copolymer that has mechanical properties that are more compatible with the tissue, such as the myocardium, into which the stent is implanted. For example, the copolymer can have an elastic modulus of about 10 MPa or less. The copolymer can also be biodegradable. The biodegradation mechanism can occur predominantly by surface erosion, particularly after initial implantation and up to 30 days or more after implantation, which maintains the mechanical integrity of the copolymer. The copolymer can include a therapeutic agent, e.g. a restenosis inhibitor, that is released into the tissue. The copolymer can include elastic segments that degrade by surface erosion and rigid segments, with higher elastic moduli, that degrade by bulk erosion and the mechanical and degradation properties can be formed by the selection of the segments and by cross-linking. The copolymer can be provided as a layer over a stent body, e.g. made of a metal, such as a biodegradable metal.

The details of one or more embodiments are set forth in the accompanying drawings and the description below. Other features, objects, and advantages will be apparent from the description and drawings, and from the claims.

DESCRIPTION OF DRAWINGS

FIG. 2A is a perspective view of an embodiment of a stent, while

DETAILED DESCRIPTION

Figure 1A:
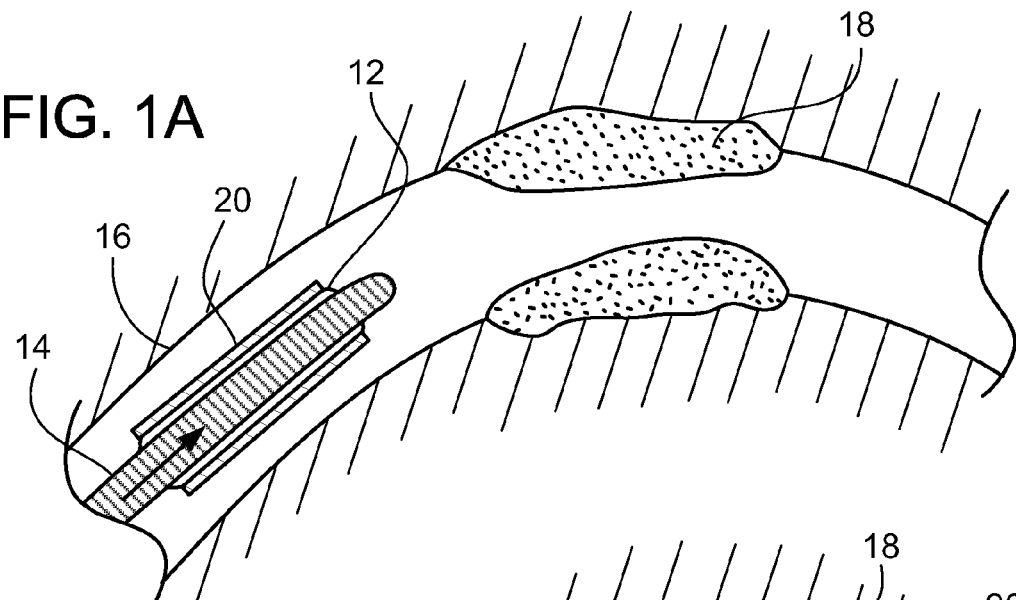
FIGS. 1A-1C are sequential, longitudinal cross-sectional views, illustrating delivery of an endoprosthesis in a collapsed state, expansion of the endoprosthesis, and the deployment of the endoprosthesis in a body lumen.
Figure 1B:
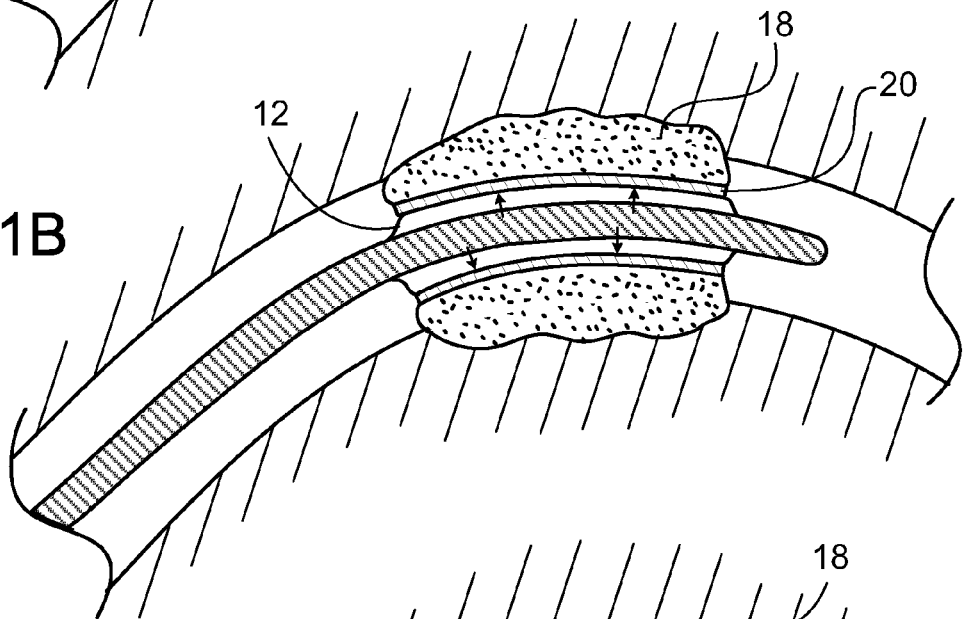
Figure 1C:
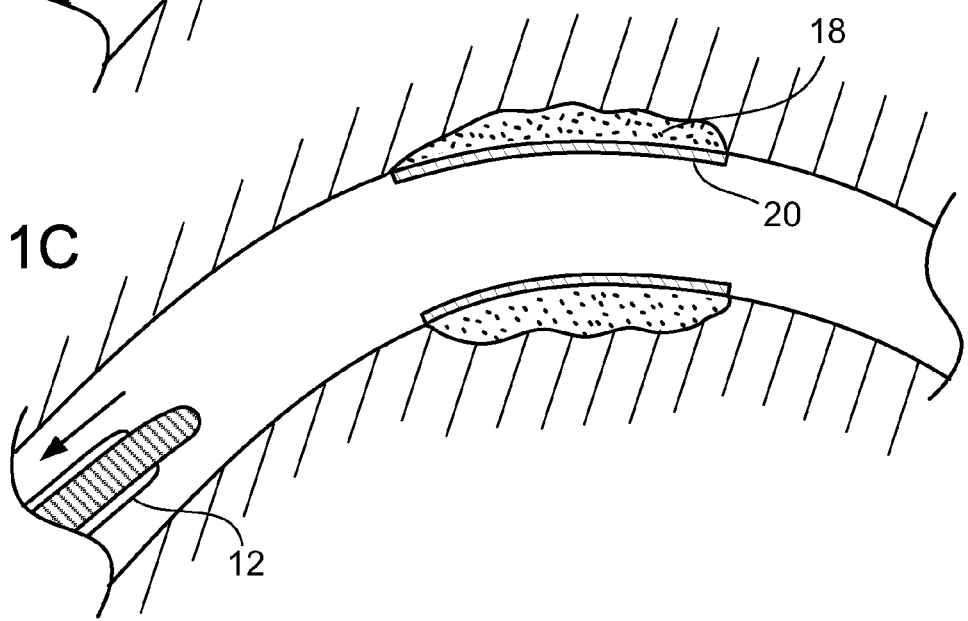

Referring to FIGS. 1A-1C, a stent 20 is placed over a balloon 12 carried near a distal end of a catheter 14, and is directed through the lumen 16 (FIG. 1A) until the portion carrying the balloon and stent reaches the region of an occlusion 18. The stent 20 is then radially expanded, e.g. by inflating the balloon 12, and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2A:
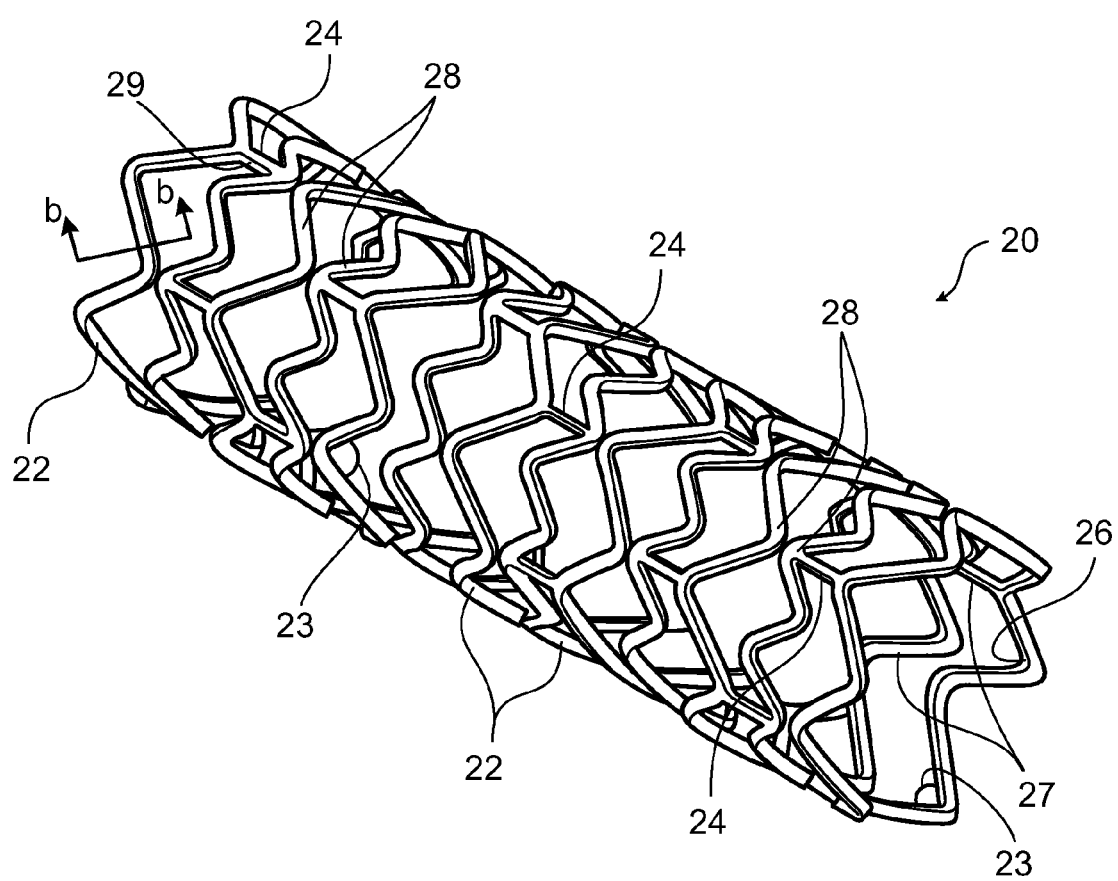

Referring to FIG. 2A, an expandable stent 20 can have a stent body having the form of a tubular member defined by a plurality of bands 22 and a plurality of connectors 24 that extend between and connect adjacent bands. During use, bands 22 can be expanded from an initial, smaller diameter to a larger diameter to contact stent 20 against a wall of a vessel, thereby maintaining the patency of the vessel. Connectors 24 can provide stent 20 with flexibility and conformability that allow the stent to adapt to the contours of the vessel. One or more bands 22 form acute angles 23. The angle 23 increases upon expansion of the stent. Stent body 20, bands 22 and connectors 24 can have a luminal surface 26, an abluminal surface 28, and a sidewall surface 29. In embodiments, the bands and/or connectors, have a width, W, and a thickness, T, of about 50 to 150 microns.

Figure 2B:
FIG. 2B is a cross-section along line bb.

Referring to FIG. 2B, the stent body 30 can carry a coating 32 including a therapeutic agent which is released to, for example, inhibit restenosis. The coating can have a thickness, Tc. In embodiments, the coating can carry substantial loading of drug and exhibit desirable agent release profiles, such as zero order release. As a result, the thickness Tc can be quite thin, which provides for a low overall profile, good adhesion to the stent body surface, and less foreign material introduced in the body. In embodiments, the thickness Tc of the coating is about 10 μm or less, e.g. 5 μm or 1 μm or less. In particular embodiments, the coating is biodegradable. In FIG. 2B, the coating is illustrated on the abluminal surface. In embodiments, the coating may instead or in addition be on the luminal and/or side wall surfaces.

Figure 3:
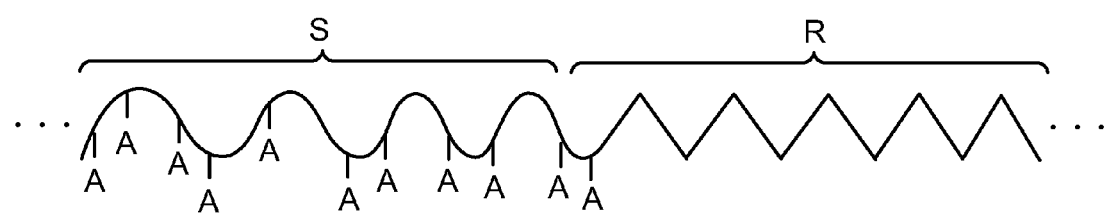
FIG. 3 is a schematic of a copolymer.

Referring to FIG. 3, the coating is a copolymer that is formed of soft segments, S, and rigid segments, R. The rigid segments, as a homopolymer, may have an elastic modulus of about 200 MPa or more, e.g. 400 MPa or more and 5000 MPa or less and may exhibit degradation by bulk erosion. The copolymer, however, is relatively flexible, having in embodiments an elastic modulus of about 20 MPa or less, e.g. about 10 or 5 MPa or less and 0.1 MPa or more. The copolymer also exhibits degradation by surface erosion. The relatively low elastic modulus enhances the compatibility of the polymer with adjacent tissue, while degradation by surface erosion maintains the mechanical integrity of the polymer for a substantial period (e.g., 30 days or more, 60 days or more, 90 days or more). The mechanical properties, erosion characteristics, and drug delivery profile can be adjusted by selecting the segments, by adjusting the length of the segments, and/or by selecting a degree of cross-linking. The copolymer can be functionalized with groups A, to enhance adhesion to a metal surface, e.g. with an anhydride, such as maleic anhydride.

Suitable soft segments include trimethyl carbonates (TMC), such as 1,3 trimethyl carbonate. Suitable rigid segments include lactides, e.g. polylactic acid (PLA), glycolides, e.g. poly(lactic-co-glycolic) acid (PLGA), and polycaprolactones (PCL). The copolymers can be formed by open ring polymerization and can be cross-linked by gamma radiation. Suitable copolymers, synthesis techniques and techniques for measuring mechanical and degradation properties are provided in Bat et al., Biomacromolecules 2008, 9, 3209. The copolymer can be functionalized to enhance adhesion by incorporating certain amino acids, such as dihydroxyphenylalanine (DOPA). Functionalization of polymers with DOPA is described in, for example, in U.S. Provisional patent application Ser. No. 61/334,691, filed concurrently with the present application. The polymer can be formed directly on a stent surface or preformed and then bonded, e.g. by melt bonding, onto the stent surface. Therapeutic agent can be incorporated during polymerization or subsequently, for example, by soaking, mixing, and/or adsorbing.

Figure 4A:
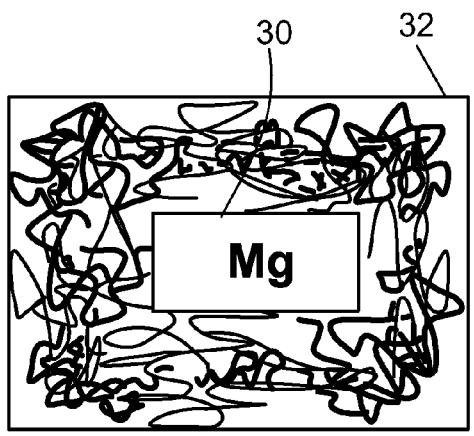
FIGS. 4A-4C are schematic cross-sections bb in FIG. 2A through a portion of a stent body.
Figure 4B:
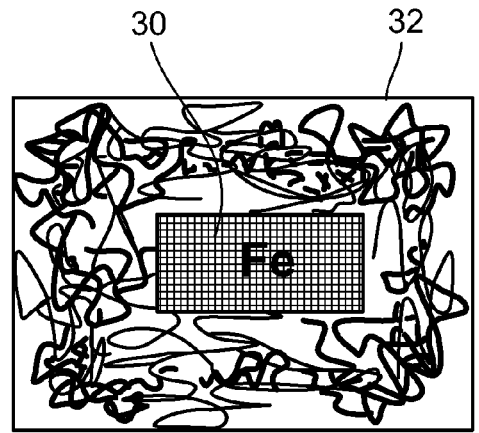
Figure 4C:
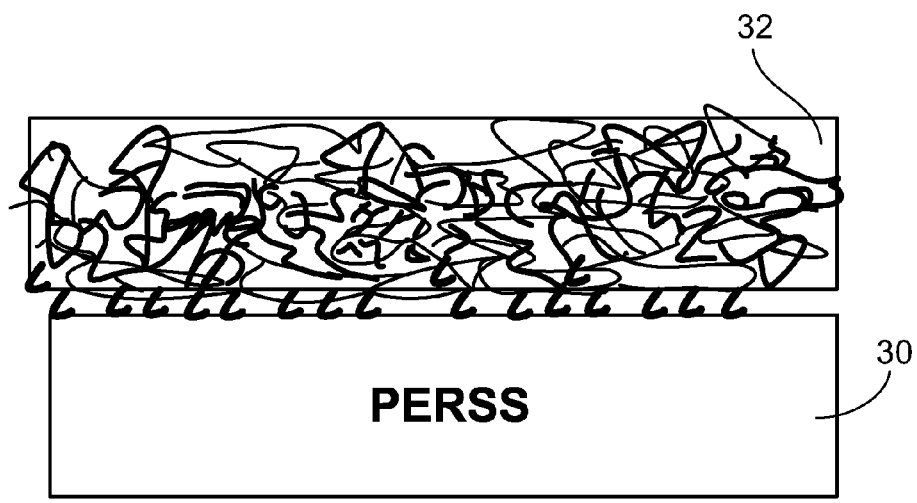

Referring to FIGS. 4A-4C, embodiments are illustrated. Referring particularly to FIG. 4A, a stent body 30 has a coating 32 of a copolymer that includes rigid segments that degrade by bulk hydrolysis (e.g. PLA, PLGA or PCL); and rubbery segments (e.g., poly-tri-methylene carbonate) that degrade by enzymatic surface erosion and can be cross-linked by irradiation. The copolymer can be formulated with therapeutic agents, such as paclitaxel and its analogues. The copolymer can be provided as coating on a biodegradable magnesium stent body. In some embodiments, enzymatic surface erosion occurs by lipase action (e.g., endothelial lipase action). Degradation of copolymers by lipases is described, for example, in Bat et al., Biomacromolecules 2008, 9, 3209, herein incorporated by reference in its entirety. Further, as atherosclerotic blood vessels can have increased endothelial lipase expression, the copolymer can have enhanced surface degradation via lipase action. The role of endothelial lipase in atherosclerosis is described, for example, in Ishida T. et al., J. Biol. Chem. (2004), 279(43), 45085-45092, herein incorporated by reference in its entirety.

Referring to 4B, stent body 30 has a coating 32 of a copolymer that includes rigid segments (e.g., PLA, PLGA or PCL) that degrade by bulk hydrolysis, and rubbery segments (e.g., poly-tri-methylene carbonate) that are relatively resistant to hydrolysis but is susceptible to degradation by enzymatic surface erosion. The segments can be cross-linked by irradiation. The copolymer can be provided as a coating on an biodegradable iron stent body. Referring to FIG. 4C, the stent body 30 has a coating 32 of a copolymer that includes rigid segments that degrade by bulk hydrolysis (e.g., PLA, PLGA or PCL) and rubbery segments (e.g., poly-tri-methylene carbonate (PTMC)) that degrade by enzymatic surface erosion. The segments can be cross-linked by irradiation. The copolymer can be provided on a biostable metal stent body (e.g. a stainless steel stent or a Co—Cr stent). The rubbery segments (e.g., PTMC segments) can be functionalized with maleic anhydride for abluminal surface adhesion. Examples of polymer functionalization with maleic anhydride and their characterization are described, for example, in Li et al., polymer 43 (2002) 5455-5461, herein incorporated by reference in its entirety. The copolymer can be formulated with therapeutic agents, such as paclitaxel and its analogues. In some embodiments, the copolymer can be provided as a coating on a biodegradable polymeric stent, such as a stent including polylactic acid, and/or poly(tyrosine carbonate).

In some embodiments, the copolymer is intimately mixed with one or more inorganic materials, such as hydroxyapatite, to form a hybrid organic-inorganic material. The hybrid material can be in the form of, for example, interpenetrating networks, intercalated layered materials or frameworks, or blends. The inorganic materials can include, for example, hydroxyapatite, silica, titania, ferrite, zeolites, and molecular sieves. The particles can be encapsulated in a polymeric shell (e.g., a copolymeric shell), surface functionalized and reacted with a polymer (e.g., a copolymer), blended with a polymer, or self-assembled with a polymer. Examples of hybrid organic-inorganic materials are described, for example, in Kickelbick G., Prog. Polym. Sci. 28 (2003) 83-114, herein incorporated by reference in its entirety.

Other Embodiments

A stent is bioerodible if the stent or a portion thereof exhibits substantial mass or density reduction or chemical transformation, after it is introduced into a patient, e.g., a human patient. Mass reduction can occur by, e.g., dissolution of the material that forms the stent and/or fragmenting of the stent. Chemical transformation can include oxidation/reduction, hydrolysis, substitution, and/or addition reactions, or other chemical reactions of the material from which the stent or a portion thereof is made. The erosion can be the result of a chemical and/or biological interaction of the stent with the body environment, e.g., the body itself or body fluids, into which it is implanted. The erosion can also be triggered by applying a triggering influence, such as a chemical reactant or energy to the stent, e.g., to increase a reaction rate. For example, a stent or a portion thereof can be formed from an active metal, e.g., Mg or Fe or an alloy thereof, and which can erode by reaction with water, producing the corresponding metal oxide and hydrogen gas; a stent or a portion thereof can also be formed from a bioerodible polymer, or a blend of bioerodible polymers which can erode by hydrolysis with water. Fragmentation of a stent occurs as, e.g., some regions of the stent erode more rapidly than other regions. The faster eroding regions become weakened by more quickly eroding through the body of the endoprosthesis and fragment from the slower eroding regions.

Preferably, the erosion occurs to a desirable extent in a time frame that can provide a therapeutic benefit. For example, the stent may exhibit substantial mass reduction after a period of time when a function of the stent, such as support of the lumen wall or drug delivery, is no longer needed or desirable. In certain applications, stents exhibit a mass reduction of about 10 percent or more, e.g. about 50 percent or more, after a period of implantation of about one day or more, about 60 days or more, about 180 days or more, about 600 days or more, or about 1000 days or less. Erosion rates can be adjusted to allow a stent to erode in a desired sequence by either reducing or increasing erosion rates. For example, regions can be treated to increase erosion rates by enhancing their chemical reactivity, e.g., coating portions of the stent with a silver coating to create a galvanic couple with the exposed, uncoated Iron surfaces on other parts of the stent. Alternatively, regions can be treated to reduce erosion rates, e.g., by using coatings.

A coating can be deposited or applied over the surface of stent to provide a desired function. Examples of such coatings include a tie layer, a biocompatible outer coating, a radiopaque metal or alloy, and/or a drug-eluting layer.

A stent can be incorporated with at least one releasable therapeutic agent, drug, or pharmaceutically active compound to inhibit restenosis, such as paclitaxel, or to treat and/or inhibit pain, encrustation of the stent or sclerosing or necrosing of a treated lumen. The therapeutic agent can be a genetic therapeutic agent, a non-genetic therapeutic agent, or cells. The therapeutic agent can also be nonionic, or anionic and/or cationic in nature. Examples of suitable therapeutic agents, drugs, or pharmaceutically active compounds include anti-thrombogenic agents, antioxidants, anti-inflammatory agents, anesthetic agents, anti-coagulants, and antibiotics, as described in U.S. Pat. No. 5,674,242; U.S. Ser. No. 09/895,415, filed Jul. 2, 2001; U.S. Ser. No. 11/111,509, filed Apr. 21, 2005; and U.S. Ser. No. 10/232,265, filed Aug. 30, 2002, the entire disclosure of each of which is herein incorporated by reference. Representative conventional approaches disperse the therapeutic agent, drug, or a pharmaceutically active compound in a polymeric coating carried by a stent. In the present invention, the therapeutic agent, drug, or a pharmaceutically active compound can be directly incorporated into the pores generated by plasma immersion ion implantation treatment on the surface of a stent, thereby eliminating the use of extra coatings.

Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; proteins; gene therapies; nucleic acids with and without carrier vectors (e.g., recombinant nucleic acids, DNA (e.g., naked DNA), cDNA, RNA, genomic DNA, cDNA or RNA in a non-infectious vector or in a viral vector which may have attached peptide targeting sequences, antisense nucleic acids (RNA, DNA)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules).

Non-limiting examples of therapeutic agents include anti-thrombogenic agents; thrombogenic agents; agents that promote clotting; agents that inhibit clotting; antioxidants; angiogenic and anti-angiogenic agents and factors; anti-proliferative agents (e.g., agents capable of blocking smooth muscle cell proliferation, such as rapamycin); calcium entry blockers (e.g., verapamil, diltiazem, nifedipine); targeting factors (e.g., polysaccharides, carbohydrates); agents that can stick to the vasculature (e.g., charged moieties, such as gelatin, chitosan, and collagen); and survival genes which protect against cell death (e.g., anti-apoptotic Bcl-2 family factors and Akt kinase).

Examples of non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, anti-thrombin antibodies, antiplatelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins;

antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Examples of genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents are disclosed in Kunz et al., U.S. Pat. No. 5,733,925, which is incorporated herein by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

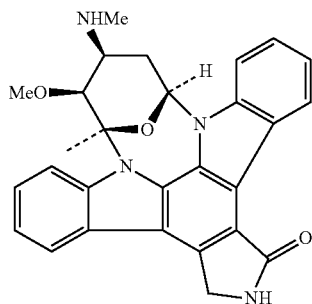 [SMILES: CN[C@H]1C[C@H]2O[C@@](C)([C@H]1OC)n1c3ccccc3c3c4c(c5c6ccccc6n2c5c31)C(=O)NC4]

as well as diindoloalkaloids having one of the following general structures:

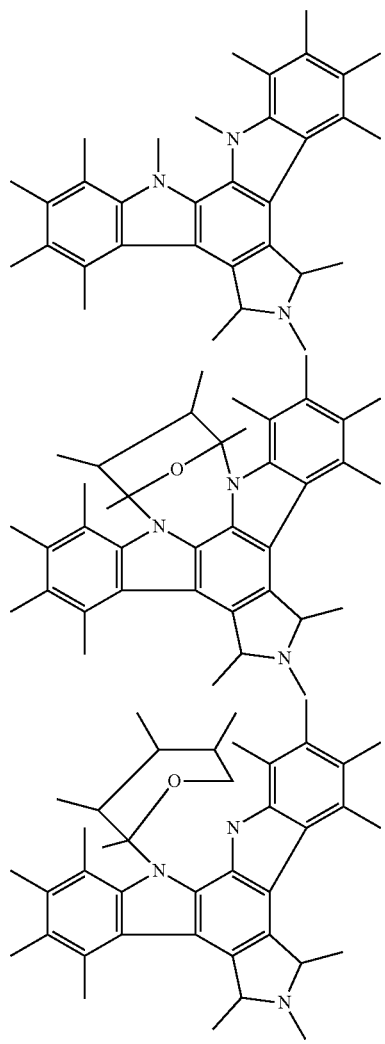

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including α-antagonists (e.g., prazosin, bunazosine), β-antagonists (e.g., propranolol), and α/β-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP Iib/IIIa inhibitors (e.g., abciximab, epitifibatide, tirofiban, intergrilin); coagulation pathway modulators, including heparinoids (e.g., heparin, low molecular weight heparin, dextran sulfate, β-cyclodextrin tetradecasulfate), thrombin inhibitors (e.g., hirudin, hirulog, PPACK (D-phe-L-propyl-L-arg-chloromethylketone), argatroban), Fxa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclins and prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-β pathway agents such as polyanionic agents (heparin, fucoidin), decorin, and TGF-β antibodies, EGF pathway agents (e.g., EGF antibodies, receptor antagonists, chimeric fusion proteins), TNF-α pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganics (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, antisense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, interleukins, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

In some embodiments, a therapeutic agent can be hydrophilic. An example of a hydrophilic therapeutic agent is doxorubicin hydrochloride. In certain embodiments, a therapeutic agent can be hydrophobic. Examples of hydrophobic therapeutic agents include paclitaxel, cisplatin, tamoxifen, and doxorubicin base. In some embodiments, a therapeutic agent can be lipophilic. Examples of lipophilic therapeutic agents include taxane derivatives (e.g., paclitaxel) and steroidal materials (e.g., dexamethasone).

Therapeutic agents are described, for example, in DiMatteo et al., U.S. Patent Application Publication No. US 2004/0076582 A1, published on Apr. 22, 2004, and entitled "Agent Delivery Particle"; Schwarz et al., U.S. Pat. No. 6,368,658; Buiser et al., U.S. patent application Ser. No. 11/311,617, filed on Dec. 19, 2005, and entitled "Coils"; and Song, U.S. patent application Ser. No. 11/355,301, filed on Feb. 15, 2006, and entitled "Block Copolymer Particles", all of which are incorporated herein by reference. In certain embodiments, in addition to or as an alternative to including therapeutic agents, particle 100 can include one or more radiopaque materials, materials that are visible by magnetic resonance imaging (MRI-visible materials), ferromagnetic materials, and/or contrast agents (e.g., ultrasound contrast agents). Radiopaque materials, MRI-visible materials, ferromagnetic materials, and contrast agents are described, for example, in Rioux et al., U.S. Patent Application Publication No. US 2004/0101564 A1, published on May 27, 2004, and entitled "Embolization", which is incorporated herein by reference.

In some embodiments, the therapeutic agent is functionalized with a reactive group (e.g., functionalities 144 or 154) such that the therapeutic agent can be covalently bound to the polymer network.

The copolymer materials described above can be used for the entire stent body, or a portion of the stent body or as a layer on a stent made of another material, or can include a layer of another material, which other material may be bioerodible or biostable, a metal, a polymer or a ceramic. In some embodiments, the stent can include one or more bioerodible metals, such as magnesium, zinc, iron, or alloys thereof. The stent can include bioerodible and non-bioerodible materials. The stent can have a surface including bioerodible metals, polymeric materials, or ceramics. The stent can have a surface including an oxide of a bioerodible metal. Examples of bioerodible alloys also include magnesium alloys having, by weight, 50-98% magnesium, 0-40% lithium, 0-1% iron and less than 5% other metals or rare earths; or 79-97% magnesium, 2-5% aluminum, 0-12% lithium and 1-4% rare earths (such as cerium, lanthanum, neodymium and/or praseodymium); or 85-91% magnesium, 6-12% lithium, 2% aluminum and 1% rare earths; or 86-97% magnesium, 0-8% lithium, 2-4% aluminum and 1-2% rare earths; or 8.5-9.5% aluminum, 0.15%-0.4% manganese, 0.45-0.9% zinc and the remainder magnesium; or 4.5-5.3% aluminum, 0.28%-0.5% manganese and the remainder magnesium; or 55-65% magnesium, 30-40% lithium and 0-5% other metals and/or rare earths. Bioerodible magnesium alloys are also available under the names AZ91D, AM50A, and AE42. Other bioerodible alloys are described in Bolz, U.S. Pat. No. 6,287,332 (e.g., zinc-titanium alloy and sodium-magnesium alloys); Heublein, U.S. Patent Application 2002000406; and Park, Science and Technology of Advanced Materials, 2, 73-78 (2001), the entire disclosure of each of which is herein incorporated by reference. In particular, Park describes Mg—X—Ca alloys, e.g., Mg—Al—Si—Ca, Mg—Zn—Ca alloys. Examples of bioerodible polymers include polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly-L-lactide, poly-D-lactide, polyglycolide, poly(alpha-hydroxy acid), and combinations thereof.

A stent can also include non-bioerodible materials. Examples of suitable non-bioerodible materials include stainless steels, platinum enhanced stainless steels, cobalt-chromium alloys, nickel-titanium alloys, noble metals and combinations thereof. In some embodiments, stent 20 can include bioerodible and non-bioerodible portions. In some embodiments, non-bioerodible or biostable metals can be used to enhance the X-ray visibility of bioerodible stents. The bioerodible stent main structure of a stent can be combined with one or more biostable marker sections. The biostable marker sections can include, for example, Gold, Platinum or other high atomic weight elements. The biostable marker sections can provide enhance visibility and radiopacity and can provide a structural purpose as well.

A stent can have any desired shape and size (e.g., superficial femoral artery stents, coronary stents, aortic stents, peripheral vascular stents, gastrointestinal stents, urology stents, and neurology stents). Depending on the application, stent 20 can have an expanded diameter of about 1 mm to about 46 mm. For example, a coronary stent can have an expanded diameter of about 2 mm to about 6 mm; a peripheral stent can have an expanded diameter of about 5 mm to about 24 mm; a gastrointestinal and/or urology stent can have an expanded diameter of about 6 mm to about 30 mm; a neurology stent can have an expanded diameter of about 1 mm to about 12 mm; and an abdominal aortic aneurysm stent and a thoracic aortic aneurysm stent can have an expanded diameter of about 20 mm to about 46 mm. Stent 20 can be self-expandable, balloon-expandable, or a combination of self-expandable and balloon-expandable (e.g., as described in U.S. Pat. No. 5,366,504). Stent 20 can have any suitable transverse cross-section, including circular and non-circular (e.g., polygonal such as square, hexagonal or octagonal).

A stent can be implemented using a catheter delivery system. Catheter systems are described in, for example, Wang U.S. Pat. No. 5,195,969; Hamlin U.S. Pat. No. 5,270,086; and Raeder-Devens, U.S. Pat. No. 6,726,712, the entire disclosure of each of which is herein incorporated by reference. Commercial examples of stents and stent delivery systems include Radius®, Symbiot® or Sentinol® system, available from Boston Scientific Scimed, Maple Grove, Minn.

A stent can be a part of a covered stent or a stent-graft. For example, a stent can include and/or be attached to a biocompatible, non-porous or semi-porous polymer matrix made of polytetrafluoroethylene (PTFE), expanded PTFE, polyethylene, urethane, or polypropylene. In addition to vascular lumens, a stent can be configured for non-vascular lumens. For example, it can be configured for use in the esophagus or the prostate. Other lumens include biliary lumens, hepatic lumens, pancreatic lumens, uretheral lumens and ureteral lumens. MOF's as discussed above, e.g. as a layer for drug delivery, can be utilized on other implantable medical devices such as pacing and defibrillation leads.

All references, such as patent applications, publications, and patents, referred to herein are incorporated by reference in their entirety.

Still further embodiments are in the following claims.

What is claimed is:

1. A stent, comprising:
   a biodegradable metal stent body comprising Mg, Fe, or an alloy thereof;
   a copolymer coating disposed directly on the biodegradable metal stent body, the copolymer coating comprising elastic segments and rigid segments, the elastic segments being formed of a trimethyl carbonate polymer or copolymer that degrades by bulk hydrolysis, the rigid segments comprising a lactide, glycolide, $\epsilon$-caprolactone polymer or copolymer that degrades by enzymatic surface erosion, the copolymer coating being cross-linked, the copolymer coating having an elastic modulus of 10 MPa or less and exhibiting degradation by surface erosion over a period of 20 days or more; and
   one or more inorganic materials mixed into the copolymer coating;
   wherein the copolymer coating is functionalized with maleic anhydride.

2. The stent of claim 1 wherein the copolymer coating further comprises a therapeutic agent.

3. The stent of claim 1 wherein the biodegradable metal stent body further comprises cobalt and chromium.

4. The stent of claim 1 wherein the copolymer coating is on an abluminal surface of the stent body.

5. The stent of claim 1 wherein the rigid segments have an elastic modulus of 200 MPa or more based on a measurement of a homopolymer of rigid segments.

6. The stent of claim 5 wherein the rigid segments exhibit hydrolytic degradation by bulk erosion.

7. The stent of claim 2 wherein the therapeutic agent is paclitaxel.

8. A stent, comprising:
   a biodegradable metal stent body comprising Mg, Fe, or an alloy thereof;
   a copolymer coating disposed directly on the biodegradable metal stent body, the copolymer coating comprising elastic segments and rigid segments;
   wherein the elastic segments are formed of a trimethyl carbonate polymer or copolymer that degrades by bulk hydrolysis;
   wherein the rigid segments comprise a lactide, glycolide, $\epsilon$-caprolactone polymer or copolymer that degrades by enzymatic surface erosion;
   wherein the copolymer coating is cross-linked by irradiation;
   wherein the copolymer coating has an elastic modulus of 20 MPa or less and exhibits degradation over a period of 20 days or more; and
   a therapeutic agent incorporated into the copolymer coating;
   wherein the elastic segments are functionalized with maleic anhydride for abluminal surface adhesion.

9. The stent of claim 8, wherein the therapeutic agent includes paclitaxel.

10. A stent, comprising:
    a biodegradable metal stent body comprising iron;
    a copolymer coating disposed directly on the biodegradable metal stent body, the copolymer coating comprising elastic segments and rigid segments;
    wherein the elastic segments are formed of a trimethyl carbonate polymer or copolymer that degrades by bulk hydrolysis;
    wherein the rigid segments comprise a lactide, glycolide, $\epsilon$-caprolactone polymer or copolymer that degrades by enzymatic surface erosion;
    wherein the copolymer coating is cross-linked by irradiation;
    wherein the copolymer coating has an elastic modulus of 20 MPa or less and exhibits degradation over a period of 20 days or more; and
    a therapeutic agent incorporated into the copolymer coating;
    wherein the elastic segments are functionalized with maleic anhydride for abluminal surface adhesion.

11. The stent of claim 10, wherein the therapeutic agent includes paclitaxel.

* * * * *